United States Patent [19]

Gysi et al.

[11] Patent Number: 5,365,771
[45] Date of Patent: Nov. 22, 1994

[54] PROCESS AND APPARATUS FOR TESTING BOTTLES FOR CONTAMINATION

[75] Inventors: Peter Gysi, Bellikon; Theo Huesser, Rudolfstetten; Melchior Zumbach, Dübendorf, all of Switzerland

[73] Assignee: Elpatronic AG, Zug, Switzerland

[21] Appl. No.: 88,920

[22] Filed: Jul. 7, 1993

[30] Foreign Application Priority Data

Jul. 9, 1992 [CH] Switzerland ............... 02166/92-0
Sep. 1, 1992 [CH] Switzerland ............... 02715/92-6
Feb. 8, 1993 [CH] Switzerland ............... 00382/93-2

[51] Int. Cl.⁵ ............................... G01N 33/44
[52] U.S. Cl. ........................... 73/31.03; 73/863.33
[58] Field of Search ............. 73/23.2, 31.03, 863.33, 73/864.81

[56] References Cited

U.S. PATENT DOCUMENTS 3,266,292 8/1966 Bailey ........................ 73/31.03
3,321,954 5/1967 Bailey ........................ 73/23.2
3,357,257 12/1967 Herndon et al. ............. 73/863.33
4,791,820 12/1988 Lawrence et al. ........... 73/863.21

FOREIGN PATENT DOCUMENTS

534096A2 3/1993 European Pat. Off. .
1344848 10/1963 France .
1598415 4/1971 Germany .
8806138 10/1988 Germany .
9114357 5/1992 Germany .

*Primary Examiner*—Hezron E. Williams
*Assistant Examiner*—Joseph W. Roskos

[57] ABSTRACT

For testing bottles in particular by mass spectrometric analysis, gas samples are removed simultaneously from several bottles by means of probes. The gas samples are fed in succession and in a predetermined sequence to a mass spectrometer by a distributor unit. In this way, a single mass spectrometer is sufficient for testing a number of bottles thus substantially reducing costs in terms of money, maintenance and calibration time.

16 Claims, 6 Drawing Sheets

PROCESS AND APPARATUS FOR TESTING BOTTLES FOR CONTAMINATION

BACKGROUND OF THE INVENTION

The invention relates to a process and apparatus for testing bottles, in particular plastic bottles, conveyed along a conveyor line, for the presence of contamination, by testing gas samples taken from individual bottles.

For returnable bottles, in particular plastic bottles, such as PET bottles, which cannot be washed at high temperatures, the problem arises that contamination needs to be reliably detected so that contaminated bottles can be removed and not refilled. In particular it must be possible to detect returned bottles which a user has used for potentially hazardous substances (poisons, solvents, etc). An already known procedure is to take a gas sample from each bottle and to analyse the sample by photoionization detection (PID). This enables undesired substances present even in small traces in the bottle and/or in the plastic material to be detected. As such testing devices need to have a high throughput of bottles per minute (say 250 to 300 bottles per minute) to enable this kind of testing to be undertaken in an industrial bottling plant, a large number of individual PID units have hitherto been used in parallel in a given bottling line, with each of a corresponding number of bottles to be tested having an individual PID unit assigned to it. This involves high costs in terms of money and maintenance and calibration time.

SUMMARY OF THE INVENTION

It is therefore the basic task of the invention to provide a process and apparatus which significantly reduce cost, maintenance and calibration time. This is accomplished in a process of the type stated at the outset by simultaneously withdrawing gas from a plurality of bottles and by feeding the gas samples withdrawn, in succession and in a controlled sequence, to the inlet of a testing unit common to several bottles.

Successively feeding gas samples from several bottles simultaneously under test to a single testing unit yields the desired reduction in costs.

In a preferred way of carrying out the invention, this enables a mass spectrometer to be used as the testing unit. This allows particularly effective detection of any contaminants which may be present.

In the procedure according to the invention there is a longer transfer distance for the individual gas sample from the bottle concerned to the multiple-bottle testing unit than in the known procedure with a series of PID units located close to their respective bottles. Nevertheless it has been found that, contrary to initial expectations, there is still sufficient time for the analysis, and in particular for mass spectrometric analysis, even with the desired high bottle throughput.

Preferably, however, steps are taken to reduce or eliminate the effect of the transfer distance of the gas sample from the bottle to the testing unit. In particular gas is preferably continuously conveyed from each bottle under test to a distributor unit, which can be located relatively close to the testing unit, e.g. to the mass spectrometer. The gas flows fed to the distributor can then be despatched singly over a short distance To the mass spectrometer.

In addition, at least the conduits from the bottle to the distributor unit are preferably heated to prevent condensation, and air is preferably blown into the bottles under test in order to maximize the pickup by the gas sample of any contaminants present.

BRIEF DESCRIPTION OF THE DRAWINGS

Ways of carrying out the invention will now be explained in detail, by way of example, with reference to the drawings, in which.

DESCRIPTION OF THE PREFERRED EMBODIMENTS

Figure 1:
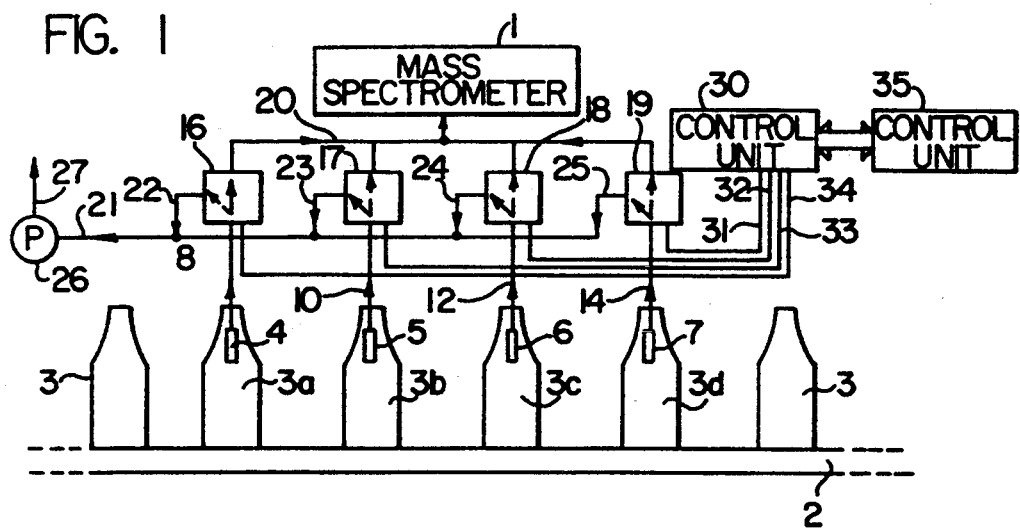
FIG. 1 is a diagrammatic representation of an apparatus for carrying out the process.

The apparatus diagrammatically illustrated in FIG. 1 has a conveyor line 2 for bottles 3. Gas samples are taken from the bottles 3a, 3b, 3c and 3d in a testing section of the conveyor line 2. This is done by lowering sampling probes 4, 5, 6 and 7 into the bottles through the bottle neck, without touching the bottle, so as to prevent any possible contamination. Gas is withdrawn from each bottle by means of the probe and is conducted via a conduit 8, 10, 12 and 14 respectively to a distributor unit with switch valves 16, 17, 18 and 19. In one position of the switch valves, the gas withdrawn from the individual bottle is fed via outlet conduits 22, 23, 24 and 25 respectively from the switch valves to a collector conduit 21. This collector conduit is connected to a suction pump 26 which pumps the gas from the individual bottle and discharges it to atmosphere via conduit 27.

While bottles 3a to 3d are present in the test line, gas is continuously extracted from the bottles by the pump 26 and supplied to the switch valves. By means of a control unit 30, which may be linked with a higher-ranking control 35, one of the valves 16 to 19 is then switched via the electrical control lines 31–34 for a predetermined period, so that the gas from the individual bottle concerned, which is flowing through the valve, passes to a second collector conduit 20 which is connected to the inlet to the testing unit 1, which may for example be a PID unit, but is preferably a mass spectrometer. Intake of gas through the conduit 20 to the mass spectrometer 1 is effected by the transfer pump incorporated in it.

After the intake of gas from one of the bottles under test, e.g. from bottle 3a, by the mass spectrometer, the valve 16 is switched again so that the flow of gas from the bottle 3a is again switched through to the outlet conduit 22. As soon as the mass spectrometer 1 is ready for the next analysis i.e. for analysis of the gas flow from the bottle 3b, the valve 17 is switched so that the gas flow from the bottle 3b passes briefly to the collector conduit 20 and thence to the mass spectrometer 1. In the same way, valves 18 and 19 are then switched briefly in succession so that gas samples from the bottles 3c and 3d can be separately analysed in succession. The probes 4 to 7 are then lifted from the bottles 3a to 3d, and another four bottles are moved up on the conveyor line 2. The probes are lowered into this new set of bottles, and gas samples are again taken. The previously tested bottles 3a to 3d are conveyed further along the conveyor line, and those bottles of this group for which an unacceptable contamination has been detected by the mass spectrometer 1 are removed from the conveyor line by a rejector device. The tested bottles which are uncontaminated then proceed, after passing through at least one washing machine, to a bottling machine where they are filled again with a drink product.

Thus, with an apparatus and/or with the process as described with reference to FIG. 1, a plurality of bottles can be tested by a single testing unit or mass spectrometer. To allow this to happen with the conveyor line 2 running at high capacity, the process is preferably performed, as described with reference to FIG. 1, if so that a gas flow is continuously supplied from each bottle to a distributor unit 16 to 19. The transfer time for the gas samples from the probes 4 to 7 through the conduits 8 to 14 is then of no consequence so far as the measurement is concerned. For the mass spectrometer 1, the individual gas sample is available at the outlet of the distributor device, or switch valves 16 to 19, that is to say, only the transfer distance through the conduit 20 to the mass spectrometer counts towards the measuring time. A large number of bottles e.g. 16 bottles with rapid transfer on the conveyor line 2, can be analysed in this way using a single mass spectrometer 1.

Further measures can be taken to assist high-speed analysis. For example, in a preferred apparatus, air is blown into the bottles during sampling in order to increase the concentration of the contaminants contained in the samples. This can preferably be accomplished by constructing the conduits 8, 10, 12 and 14 as twin conduits with sample gas extracted through one conduit as described and with air blown into the bottles through the other conduit (by means of a pump not shown in the drawing) through additional outlets in the probes 4 to 7. In addition it has proved advantageous to heat at least the sample gas conduits of the pipes 8, 10, 12 and 14 in order to prevent condensation of the sample gas on the conduit concerned. The feed conduit 20 to the mass spectrometer 1 can also be heated.

One function of the control unit 30 is to control the switching of the valves 16 to 19. In addition the control unit 30 can also control the lowering and raising of the probes 4 to 7 into and out of the individual bottles. However, this can also be effected by a higher-ranking control 35 controlling the bottle handling system as a whole, which will be explained in more detail with reference to FIG. 3. Alternatively, the controls 30 and 35 may be constructed as a combined unit. Alternatively, the lowering and raising of the probes can be performed by purely mechanical means using cam-operated lifters.

FIG. 2 shows, again in highly diagrammatic form, another embodiment of an apparatus for carrying out the process. Two testing units, or, preferably, mass spectrometers, 1 and 1a are provided. One mass spectrometer 1 is for testing bottles 3a, 3b and 3c; the other mass spectrometer 1a is for testing the bottles 3d, 3e and 3f. Thus, in this embodiment also, each individual mass spectrometer caters for several bottles tested together. The individual bottles are tested in a similar manner to that described for FIG. 1. First, e.g. bottles 3a and 3d are tested by their respective mass spectrometers 1 and 1a, as the switch valves 16 and 16a briefly switch the gas flow to the conduits 20 and 20a so that the gas sample from bottle 3a can be analysed by the mass spectrometer 1 and the gas sample from bottle 3d can be analysed by the mass spectrometer 1a. The valves are then switched back to the collector conduits 21 and 21a respectively and thence to the suction pump 26. Testing of gas samples from the bottles 3b and 3e then proceeds in a similar manner.

Figure 3:
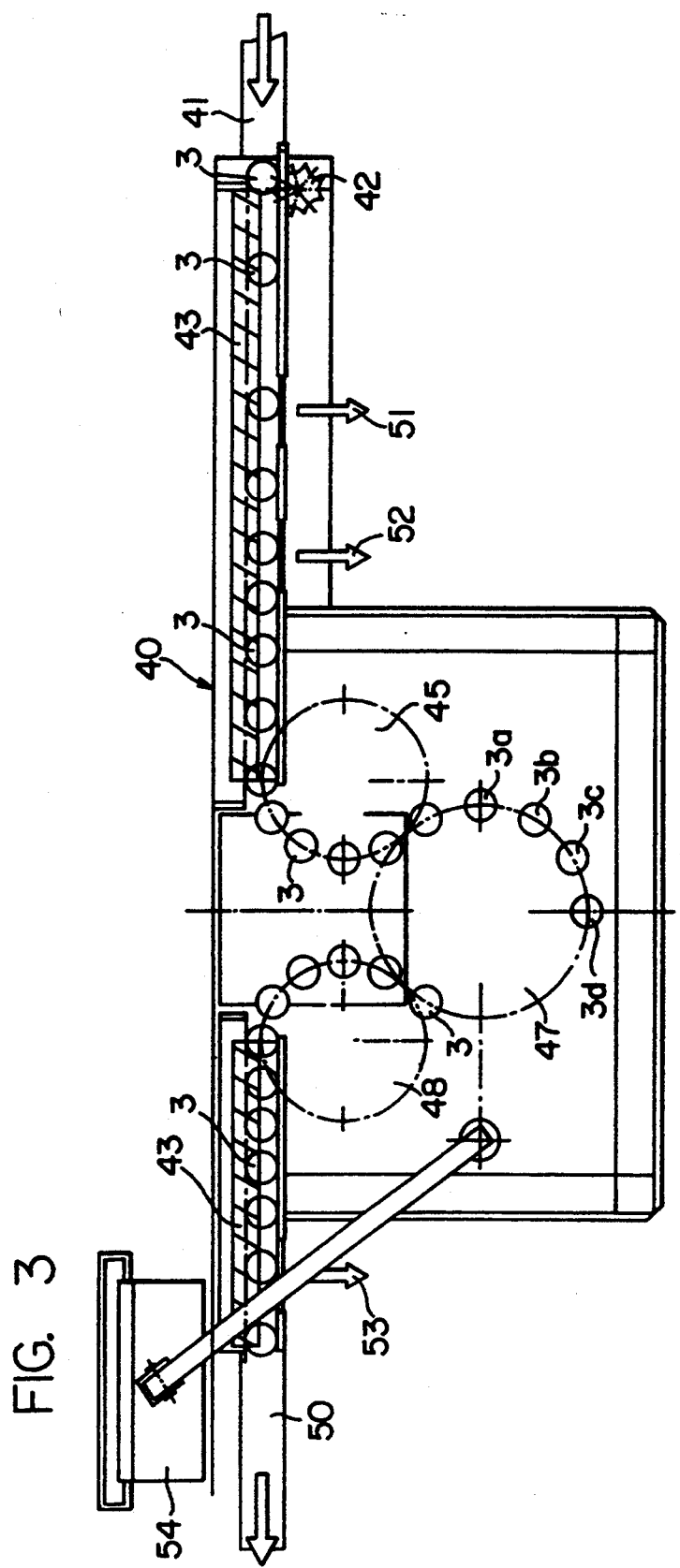
FIG. 3 is a plan view of an arrangement for carrying out the process, with several conveying means for the bottles.

FIG. 3 shows a plan view in diagrammatic form of a bottle testing apparatus 40 operating in accordance with the process. Returned bottles are randomly fed to the device on a conveyor line 41. The bottles are fed to the device in the upright position and are normally open, i.e. uncapped, and are not yet washed. By means of a conveyor and resulting backup pressure, bottles 3 are supplied to a star wheel 42 which also forms the line stop, and are also released into a worm conveyor 43 which feeds the bottles at regular intervals and in an upright position. A number of testing devices can be provided along this conveyor section 43. These will be described in detail with reference to FIG. 5. In particular, the bottles can be checked for correct height, and for the presence of a cap or other stopper and of residual liquid. Unsuitable bottles can be rejected from the worm conveyor by one of the rejectors 51 or 52. The bottles S passing these preliminary checks pass from the worm conveyor 43 on to a feed carousel 45. From this feed carousel 45 the bottles are fed to a main carousel 47. Testing, e.g. in the form of a mass spectrometric analysis, is performed while the bottles are in the main carousel 47. Only four bottles 3a to 3d are shown diagrammatically in FIG. 3. In reality the main carousel is capable of receiving a larger number of bottles to be tested, e.g. 16 bottles, which are tested by a mass spectrometer located above the main carousel.

After testing, the bottles pass via a discharge carousel 48 to a discharge worm conveyor 49. A further rejector 53 is located at this discharge worm conveyor to reject those bottles which have been identified by the mass spectrometer as contaminated. Rejection may be performed in various known ways, e.g. by means of a jet of compressed air, or by an electromechanically operated pushrod-type rejector. However, the preferred method is to use a "soft" diversion system whereby those bottles which are to be removed are guided in an upright position on to another conveyor line. In this way, overturning of bottles containing possibly harmful liquids can be avoided. These bottles are conveyed, in an upright position, to a disposal point. Downstream of the worm conveyor 49, the uncontaminated bottles are discharged to a conveyor line 50 which conveys them to a washing station and then onwards to a filling station. A control box 54 is arranged on a boom. The controls for the apparatus as a whole can be separately accommodated.

Figure 4:
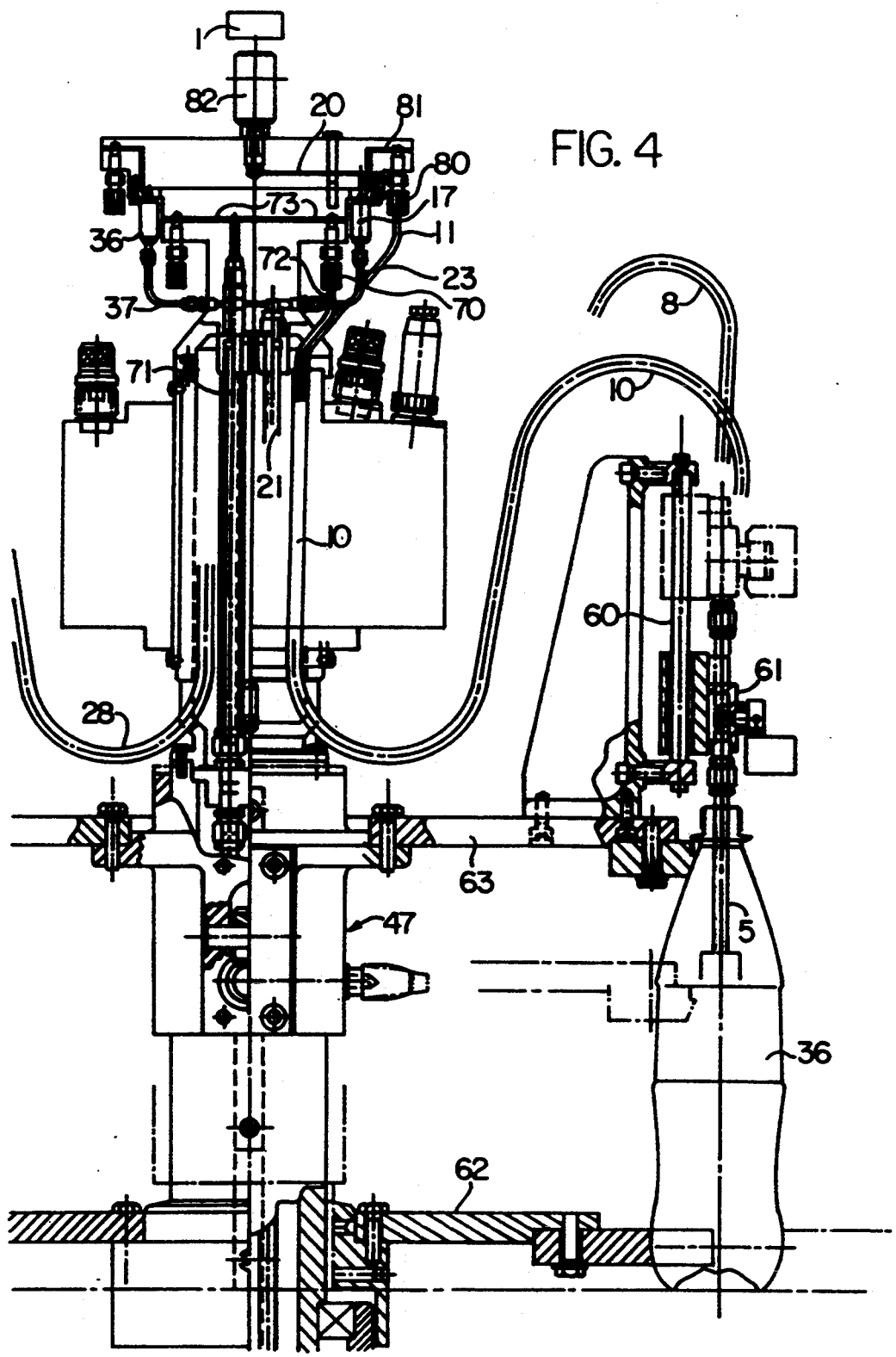
FIG. 4 shows a side view, partly in section, of part of the apparatus according to FIG. 3.

FIG. 4 shows, partly in section, a view of part of the main carousel 47 of FIG. 3. It shows a bottle 3b which is held by holding devices 62 and 63 on the carousel. The other bottles and their holding devices on the carousel are not shown in the drawing. Inserted into the bottle shown in the drawing is the probe 5 for taking the gas sample. The probe 5 is mounted on a movable carriage 61 which can be raised along a carriage guide 60 from the lower position shown in the drawing to the upper position shown in chain-dotted outline only. At the point where the bottles enter the carousel, the individual carriage 61 belonging to the holding device 63 is in the upper position. After a bottle has entered the holding device, the carriage 61 is lowered along the carriage guide 60, causing the corresponding probe to enter the bottle through the bottle neck without touching it. A hose 10 is connected to the probe 5. The connection is omitted from the drawing for the sake of clarity. When the carriage 61 is in the lower position, the line of the hose is as represented by the hose designated with the reference number 10. When the carriage 61 is in its upper position, the line of the hose is as represented by the short section 8 of the hose behind the hose 10.

The hose 10 is led to the centre of the carousel. It has a conduit 11 through which the gas sample is withdrawn from the bottle. The conduit 11 is connected by a coupling 80 to the top of the carousel. From the coupling a passageway 81 in the top of the carousel leads to the switch valve 17. One outlet of the switch valve is connected by a pipe 23 to a central pipe 21 of the carousel which leads to the suction pump 26 (FIG. 1) (not shown in FIG. 4). The other outlet of the switch valve 17 leads via the passageway 20 in the top of the carousel to a coupling 82. The carousel parts which have been mentioned so far revolve with the bottle at the same rate as the carousel. The fixed mass spectrometer 1, which is represented in merely diagrammatic form in FIG. 4 by a corresponding block, is arranged above the coupling 82. Through this coupling 82 the fixed mass spectrometer is connected to the revolving carousel i.e. to its passageways 20. The electrical control leads to the switch valves are not shown in FIG. 4. These run from the control unit via sliding contacts to the valves revolving with the carousel.

The carousel shown in FIG. 4 carries e.g. 16 receiver positions (holders) for bottles under test, and an equal number of carriages, probes, hoses, couplings, electrical switch valves and passageways 20 to the single coupling 82. In the interests of clarity, only two switch valves, the valve 17 and the valve 36, are shown in FIG. 4. The remaining elements are likewise only partly depicted, e.g. hoses 8,10 and 28. Through a central pipe 71, passageways 73, couplings 70, pipes 72 and the corresponding hoses, clean air can be blown into all bottles under test to raise the concentration of contaminants in the gas sample obtained. The flexible hoses 10 are also heated to prevent condensation of the sampled gas inside the hose.

Figure 5:
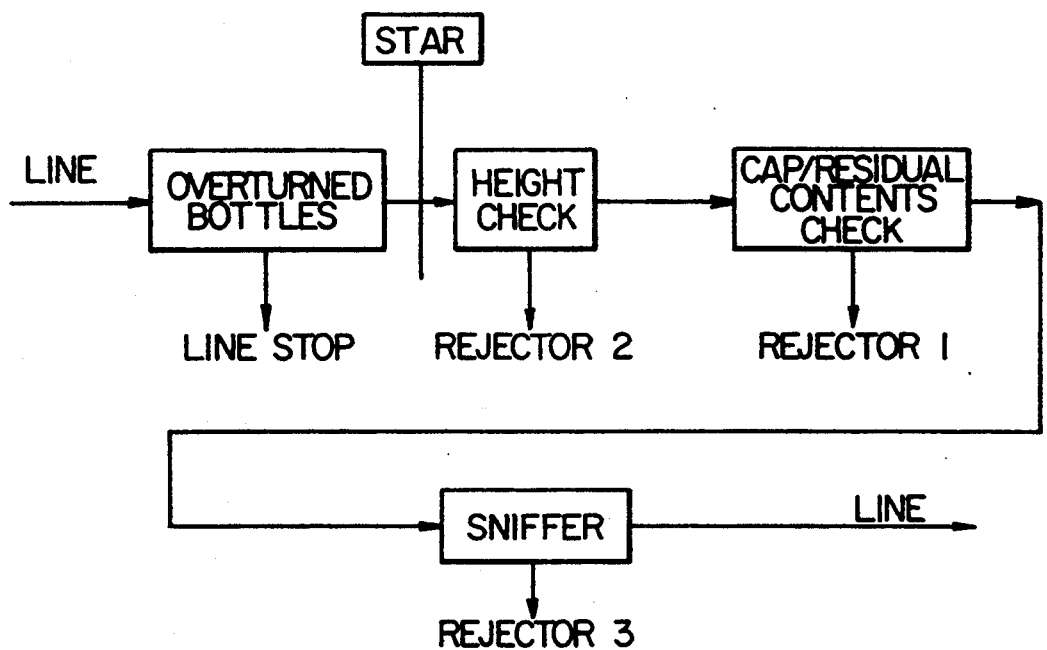
FIG. 5 is a block diagram of the steps in the testing process in the device according to FIG. 3.

FIG. 5 shows diagrammatically the steps in the testing process in the apparatus according to FIG. 3. The incoming bottles on the conveyor line arrive at the star wheel 42, where non-upright bottles cause a line stop. In the feed worm-conveyor, the height of each individual bottle is then checked by means of two photoelectric barriers. Oversize or undersize bottles are eliminated. The next check is performed by means of an ultrasonic sensor which detects whether the cap has been removed from each bottle. Bottles with caps or other stoppers are eliminated. A weight sensor is then used to check whether a relatively large quantity of residual liquid is present in the bottle. If so, the bottle is eliminated.

From the entry module the bottles pass via the feed carousel to the main carousel. On the main carousel, the sample gas is removed from the bottles and fed to the mass spectrometer or PID testing unit for analysis. The time during which a bottle remains on the carousel is much longer than the measuring time available per bottle (for comparison: the measuring time per bottle is about 240 ms whereas the time on the carousel (assuming 300 bottles per minute) is about 2 sec.).

To make full use of the relatively long period during which the bottles are on the carousel, the removal of the sample gas is performed in several stages:

| | |
|---|---|
| Stage 0 | As soon as the bottle is on the main carousel, a probe dips into the bottle to withdraw the gas sample. |
| Stage 1 from removal of gas sample to valve block. | All 16 gas sampling hoses on the main carousel are permanently drawing air into the valve block. As soon as a sampling hose is lowered into a bottle, a sample of the gas in the bottle is pumped via the hose to the valve block. Through a valve in the valve block, it is either pumped directly back to atmosphere by the air pump, or diverted to the mass spectrometer by a switching operation of the valve.<br>At any given time one of the 16 valves on the valve block is switched through to the mass spectrometer, and the others are closed and their sample gas is being discharged to atmosphere. In addition to the withdrawal of sample gas, clean air is blown into the bottles. This is in order to obtain a higher concentration of the sampling gas.<br>Lastly, all gas sampling hoses are heated to prevent condensation of the gas inside the hose. |
| Stage 2 from valve block to mass spectrometer | As already stated, one of the 16 valves is switched through at any one time. This allows the sample gas to pass from the corresponding sampling hose and its related bottle to the mass spectrometer where it can be analysed. By suitable cycled switching of the valves, every individual bottle on the carousel can be analysed in turn.<br>This 2nd stage is sequential, that is to say only one bottle can be "handled" at any given time, unlike the 1st stage in which 15 stations are "handled" in parallel, i.e. simultaneously. |

Analysis of the sample gas in the mass spectrograph finally determines whether a bottle is contaminated or not.

Instead of the electrically controlled distributor unit which has been described, a distributor unit which is entirely mechanically controlled by the rotation of the carousel can also be provided for the sample gas flows.

Figure 2:
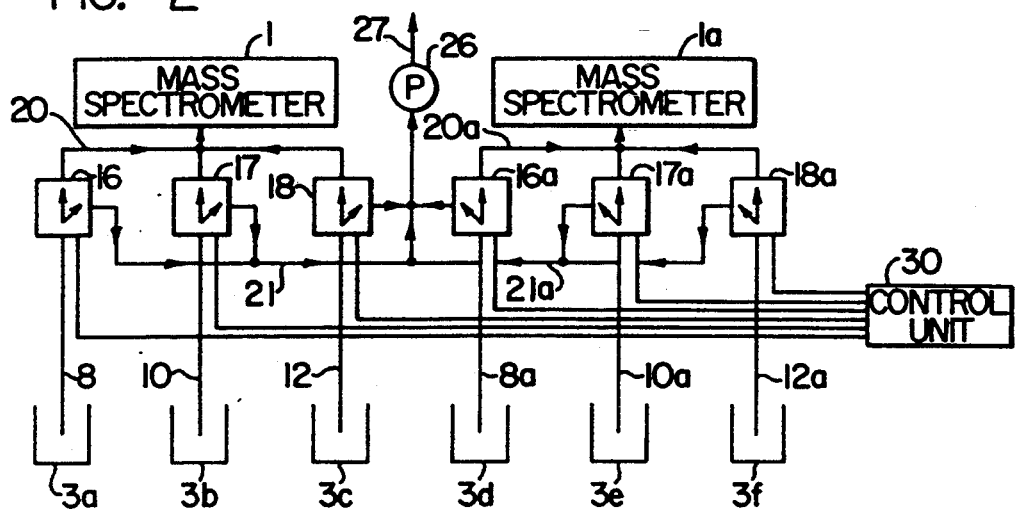
FIG. 2 is a similar representation to FIG. 1 illustrating another way of carrying out the process.

Instead of the carousel which has been described, testing can also be performed along one or more parallel or serial linear sections of a conveyor path, as illustrated in principle in FIGS. 1 and 2.

Figure 6:
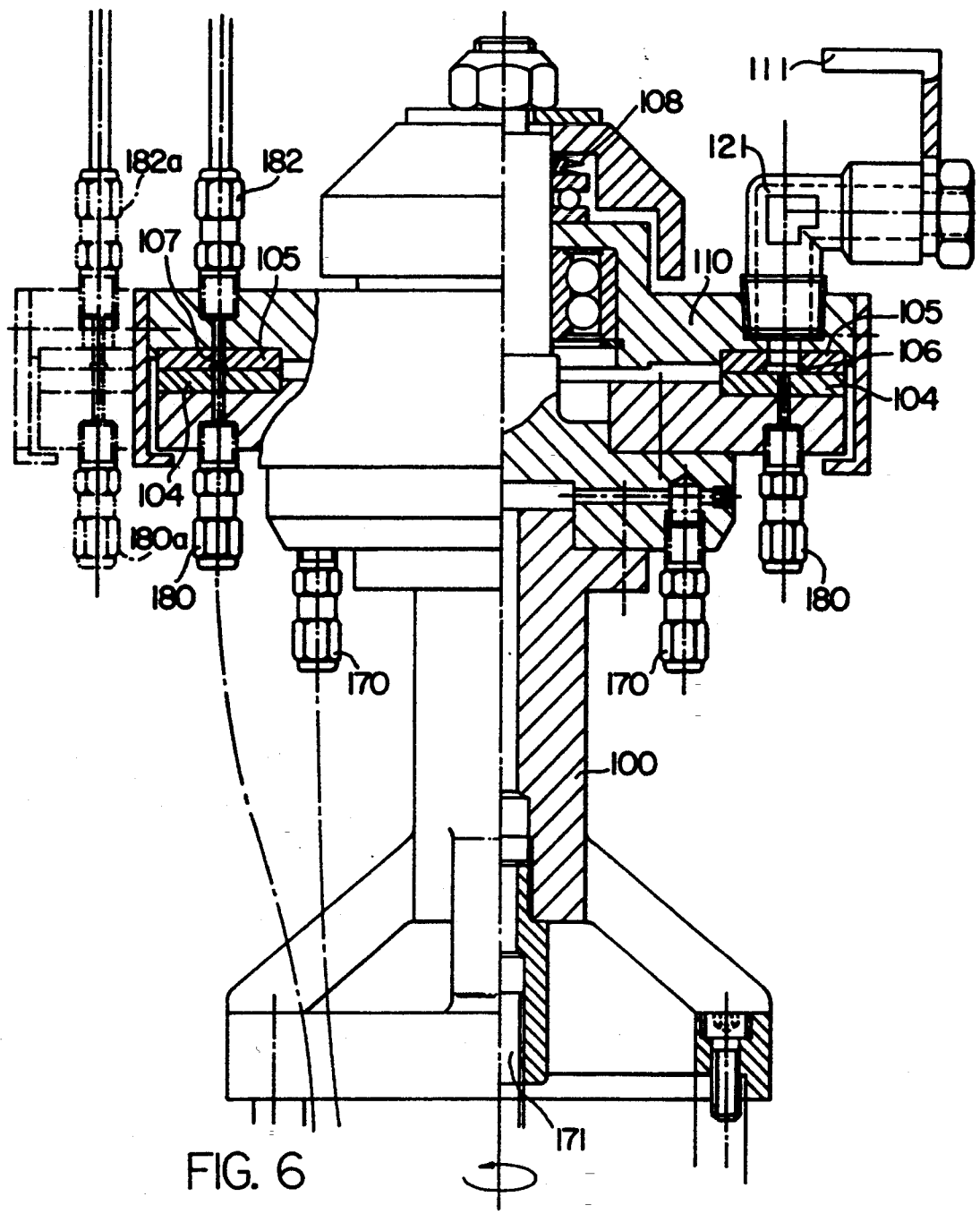
FIG. 6 shows, partly in section, a distributor unit which is modified with respect to FIG. 4.

FIG. 6 shows a mechanical distributor unit which is mounted on the carousel 47 shown in FIG. 4 in place of the electrically switched distributor unit in FIG. 4 (in FIG. 6 the carousel 47 has been omitted). The mechanical distributor unit has a lower rotating part 100 which is connected to the rotational axis of the carousel 47. This part 100 rotates with the carousel and with the bottles. The rotating part 100 carries a plurality of connections 180 for the pipes 11 (shown in FIG. 4 but not FIG. 6). Through these connections, the gas samples pass into the interior of the distributor unit. A stationary part 110 with rotation preventer 111 is arranged axially above the rotating part 100. From this stationary part 110 a connection 121 leads to the suction pump 26 (shown in FIG. 1 but not FIG. 6), which continuously sucks air (gas samples) from the bottles. From the stationary part, another connection 182 leads to the stationary mass spectrometer 1 (not shown in FIG. 6). If a second mass spectrometer 1a is provided, a corresponding connection 182a is provided.

Figure 7:
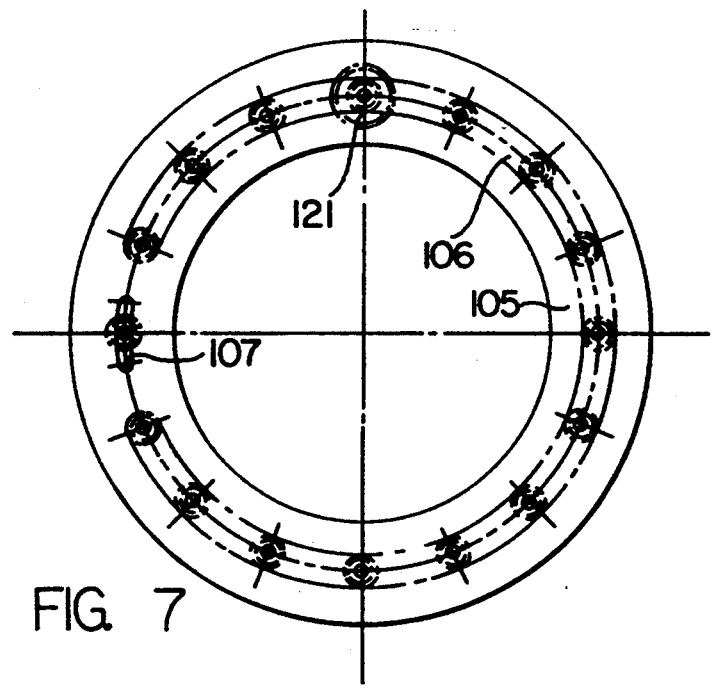
FIG. 7 is a plan view of one of the sealing faces of FIG. 6.

The rotating part 100 and the stationary part 110 slide on one another on sealing faces 104 and 105 respectively. The distributor chambers are provided in one or both of the sealing faces 104,105. A first distributor chamber 106 in the sealing face 105 serves as extraction chamber and is in permanent communication with the suction pump via the connection 121. A second distributor chamber 107 serves as linking chamber for the gas sample to be supplied to the testing unit 1 and is in permanent communication with the connection 182. The extraction chamber 106 is in the form of a circular arc (FIG. 7) and communicates via through-bores with all connections 180 and their respective pipes 11 and bottles, except for a single connection 180, shown in the left half of the drawing in FIG. 6, which is in communication with the linking chamber 107. Through this connection 180, the gas sample withdrawn from the corresponding bottle via the pipe 11 is dispensed through the chamber 107 and the connection 182 to the mass spectrometer. The gas samples from all other bottles pass via the chamber 106 and the connection 121 to the suction pump and out to atmosphere. The rotation of the carousel, and with it the lower part of the distributor unit, brings each connection 180 in succession into communication with the chamber 107 and thus with the mass spectrometer, while the other connections 180 stay in communication with the chamber 106.

Figure 8:
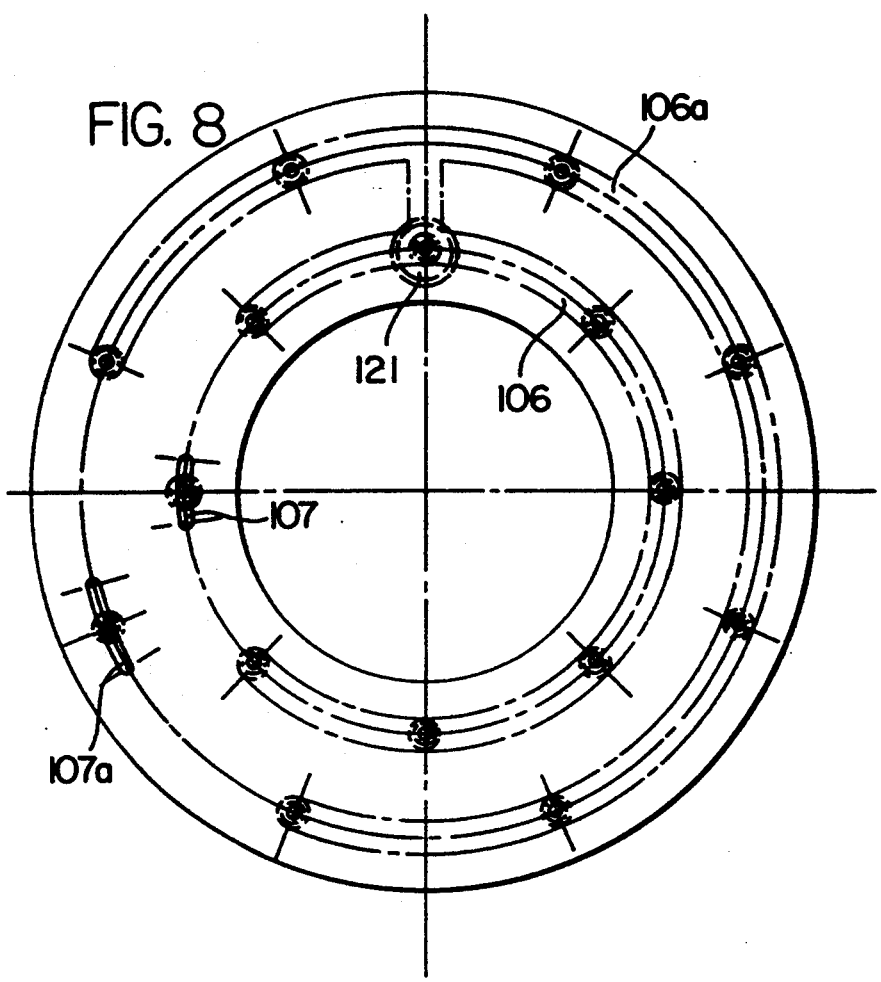
FIG. 8 is a plan view of a sealing face with another configuration.

If two mass spectrometers 1 and 1a are used, a second chamber arrangement 106a,107a can be provided, as indicated in chain-dotted outline in FIG. 8. The extraction chambers 106 and 106a may communicate i.e. be connected to the same pump connection 121. The chambers 107,107a, on the other hand, are separate, each being connected to its respective mass spectrometer 1 or 1a. A doubled processing capacity is thus obtained.

The sealing faces 104,105 are fabricated and finished as minimum-wear dry-bearing mating faces, e.g. as hard metal sliding faces on both sides, or as copper sliding faces on both sides, or as a hard metal sliding face on one side mating with a ceramic sliding face. In the illustrated embodiment the sliding faces can easily be replaced. To obtain a good seal between the sealing faces 104,105 the two parts 100,110 of the distributor unit are axially loaded by means of a ball-mounted spring 108. A central fastening allows rapid assembly or dismantling of the distributor unit.

For the individual gas sample fed to the mass spectrometer, the illustrated arrangement provides a short, straight path, reducing the memory effect.

To supply the air for injection into the bottles, the illustrated example is provided with a central duct 171 which opens into connections 170 to which the pipes for the heated flexible hoses 10 are connected.

We claim:

1. Process for testing bottles, in particular plastic bottles, conveyed along a conveyor line, for the presence of contamination, comprising the steps of;
   feeding a plurality of bottles from a conveyor line to a carousel;
   inserting one of a plurality of sampling lines into one of a plurality of bottles as the bottles enter the carousel, each of the plurality of sampling lines being connected by a distribution unit to a common suction pump;
   simultaneously and continuously withdrawing a plurality of gas samples from the plurality of bottles which are present on the carousel by means of the suction pump and the plurality of sampling lines;
   during the step of withdrawing gas introducing air into each of the bottles present on the carousel by means of an air pump and a plurality of air lines introduced into the bottles;
   feeding the plurality of gas samples, one at a time in succession and in a controlled sequence, through the distribution unit to the inlet of a testing unit common to several bottles while discharging the other of the plurality of gas samples from a bottle into the atmosphere;
   removing the sampling lines and the air lines from each of the bottles when a gas sample from a bottle has reached the testing units; and
   feeding the bottle to another conveyor line from the carousel.

2. Process according to claim 1, characterized that a mass spectrometer is provided as the testing unit.

3. Process according to claim 1, characterized by checking for the presence of residual liquid in each bottle to resting of a gas sample, and removing a bottle containing a quantity of liquid in excess of a preselected limit without withdrawing a gas sample from the bottle.

4. Process according to claim 3, characterized by removing a bottle which is to be eliminated from the conveyor line following a check and conveying the bottle to a disposal point in an upright position.

5. An apparatus for testing bottles for the presence of contamination by testing gas samples taken from individual bottles characterized by: a bottle conveyor; the conveyor including a carousel for the bottles; a number of sampling heads which can be inserted into the bottles simultaneously while under test on the conveyor, conduits connected to the respective sampling heads and a distributor unit having connections with the conduits and controlled by the rotational movement of the carousel, suction means for drawing gas samples simultaneously from the sampling heads through the conduits and the distributor unit, and at least one testing unit connected with the distributor unit for testing the gas samples sequentially.

6. An apparatus according to claim 5, characterized in that the sampling heads are constituted by suction conduits each mounted on a vertically slidable carriage.

7. An apparatus according to claim 5, characterized in that the conduits are at least partly made in the form of hoses which can be heated.

8. An apparatus according to claim 5, characterized in that the distributor unit is provided on the axis of rotation of the carousel and comprises a stationary part which is connected to the testing unit and the suction means and a rotatable part to which the conduits to the sampling heads are connected.

9. An apparatus according to claim 8, characterized in that the stationary and rotatable parts are axially loaded against one another and bear against one another at circular dry-bearing sealing faces.

10. An apparatus according to claim 9, characterized in that the sealing faces are constituted by hard metal/- hard metal, copper/copper or hard metal/ceramic dry-bearing sliding faces.

11. An apparatus according to claim 5, characterized by means for blowing air into the bottles to be tested.

12. An apparatus according to claim 5, characterized in that a bottle height testing arrangement, residual contents testing device, cap checking arrangement and bottle rejector means are located upstream of of the sampling heads in the conveying direction.

13. Apparatus according to claim 12, characterized in that the bottle ejector means comprise conveyor means which remove rejected bottles from the conveyor in an upright position.

14. Apparatus according to claim 5, characterized in that the distributor unit includes a plurality of electrical switch valves for connecting a given sampling head via a conduit with the suction means in the first switching position, and with the testing unit in the second switching position.

15. Apparatus according to claim 5, characterized in that the conveyor has at least one linear conveyor section along which the sampling heads, conduits and the distributor unit are arranged.

16. An apparatus for testing bottles for the presence of contamination by testing gas samples taken from individual bottles comprising: a bottle conveyor, which includes a carousel, and a number of sampling heads arranged on the carousel and inserted into the bottles under test on the conveyor; conduits connected to the respective sampling heads; a distributor unit having connections for the conduits and arranged on the carousel; suction means for drawing gas samples from the sampling heads through the conduits and the distributor unit and at least one testing unit, connected with the distributor unit.

* * * * *

UNITED STATES PATENT AND TRADEMARK OFFICE
CERTIFICATE OF CORRECTION

PATENT NO. : 5,365,771

DATED : November 22, 1994

INVENTOR(S) : Peter Gysi, Theo Huesser, Melchior Zumbach

It is certified that error appears in the above-identified patent and that said Letters Patent is hereby corrected as shown below:

Column 8,

Claim 3:

Line 3, delete "resting" and substitute --testing--,
    Line 3, before "to" insert --prior--.

Signed and Sealed this

Fourteenth Day of February, 1995

*Attest:*

BRUCE LEHMAN

*Attesting Officer*     *Commissioner of Patents and Trademarks*